United States Patent [19]

Kaura

[11] Patent Number: 5,663,701
[45] Date of Patent: Sep. 2, 1997

[54] STOMACH DEBRIS COLLECTING MAGNET

[76] Inventor: Kamaljit S. Kaura, 30 Coronado Pointe, Laguna Niguel, Calif. 92677

[21] Appl. No.: 698,036

[22] Filed: Aug. 15, 1996

[51] Int. Cl.$^6$ .............................. H01F 7/02; A61M 37/00
[52] U.S. Cl. .............................. 335/306; 600/12
[58] Field of Search .............................. 335/302–306; 600/9, 12; 210/222

[56] References Cited

U.S. PATENT DOCUMENTS

| | | | |
|---|---|---|---|
| 3,206,657 | 9/1965 | Moriya | 317/201 |
| 4,283,698 | 8/1981 | Fujisawa | 335/306 |
| 4,303,062 | 12/1981 | Vars | 128/1.3 |
| 4,544,904 | 10/1985 | Tarachand | 335/302 |
| 4,992,768 | 2/1991 | Mozis et al. | 335/306 |
| 5,096,763 | 3/1992 | Ogata et al. | 428/76 |

*Primary Examiner*—Lincoln Donovan
*Assistant Examiner*—Raymond M. Barrera
*Attorney, Agent, or Firm*—Gene Scott - Patent Law & Venture Group

[57] ABSTRACT

An elongated magnetic assembly has an outer case enclosed by two end caps all of a non-magnetic, corrosion resistant and highly rigid structural material. The interior of the case provides a pair of magnets separated by an iron bearing spacer having contact with magnetic pole surfaces of the magnets. Two iron bearing pole keepers are place on the opposing pole surfaces of the magnets. The magnetic circuit is such that the device attracts debris forming a ball over time so that there is less likelihood of a sharp objects puncturing the stomach wall of the animal.

3 Claims, 2 Drawing Sheets

STOMACH DEBRIS COLLECTING MAGNET

BACKGROUND OF THE INVENTION

1. Field of the Invention

This invention relates generally to permanent magnets and more particularly to an advanced animal pill type magnet for improved collecting of iron bearing debris in the stomach of farm animals.

2. Description of Related Art

The following art defines the present state of this field:

Ogata, U.S. Pat. No. 5,096,763 describes a magnet article for attracting foreign matters in the stomach that is constituted by a hollow cylindrical case made of a corrosion-resistant, non-magnetic material: a plurality of disc-shaped yokes made of a soft magnetic material; a plurality of disc-shaped magnet members made of an R-Fe-B permanent magnet material and having magnetic poles on both end surfaces, the disc-shaped yokes in the hollow cylindrical case such that the magnetic poles having the same polarity of the adjacent disc-shaped magnet members face each other via each disc-shaped yoke; and a pair of end covers made of a corrosion-resistant, non-magnetic material, each end cover being fixed to each end of the hollow cylindrical case so that the inside of the hollow cylindrical case is sealed.

Mozis et at., U.S. Pat. No. 4,992,768 describes a cow magnet to be ingested by a ruminant animal comprises a stack of cylindrical permanent magnets having intermediate disk-like spacers of a soft magnetic material where the stack is held together by first and second plastic end cap members with integrally formed tubular sleeves adapted to fit into central bores formed through the cylindrical magnets and spacers with a predetermined friction fit. A pin formed from high carbon steel is then inserted down the center of the tubular sleeves to cause them to expand and tightly engage the side wall defining the central bore formed through the stacked arrangement of magnet and spacers.

Vars, U.S. Pat. No. 4,303,062 describes a therapeutic magnet for retention in the stomach of an animal comprises a plastic coated sintered ceramic magnet. The magnet is elongate and of uniform rectangular cross section in planes transverse to its principal dimension. The direction of magnetization is transverse to the principal dimension. The plastic coating serves to retain the separate parts of the magnet in the event of inadvertent fracture of the magnet.

Fujisawa, U.S. Pat. No. 4,283,698 describes a magnet device for collecting scrap irons in the stomach that which cattle have swallowed into the stomach. The magnet device is constituted by a plurality of magnets and at least a magnetic plate interposed therebetween.

Tarachand, U.S. Pat. No. 4,544,904 describes a composite permanent magnet and a circuit which employs a plurality of such magnets. The composite magnet combines discrete sections of a first magnet material with at least one discrete section of a second magnetic material. The first material has a high residual magnetic strength and a moderate energy product. The second material is many times more expensive than the first material and is characterized by a high residual magnetic strength and a high energy product.

Moriya, U.S. Pat. No. 3,206,657 describes a magnet assembly for filtering and to an assembly of discrete magnets adapted to be placed in a fluent material to extract paramagnetic particles therefrom. An object of this invention is the provision of the filter trap for paramagnetic particles which comprise spaced apart discrete magnets arranged in a sheath of non-magnetic material. Another object is the provision of a plurality of ball or short bar magnets arranged in spaced apart relation in a flexible sheath of non-magnetic material.

The prior art teaches the use of cow magnets for use in collecting debris in animal stomachs. However, the prior art does not teach the placement of the magnetic members in such magnets so that sharp objects tend not to collect at the ends of such devices, and do not teach how to obtain a ball shape as the debris builds-up on the device over time. The ball shape is preferred in minimizing the potential for stomach punctures from the sharp ends of such collected objects. The present invention fulfills these needs and provides further related advantages as described in the following summary.

SUMMARY OF THE INVENTION

The present invention teaches certain benefits in construction and use which give rise to the objectives described below.

The present invention provides an elongated magnetic assembly having an outer case enclosed by two end caps. The interior of the case provides a pair of magnets separated by a spacer having contact with magnetic pole surfaces of the magnets. Two pole keepers are place on the opposing pole surfaces of the magnets.

A primary objective of the present invention is to provide an animal stomach magnet device that is inexpensive and yet highly effective in the collection of magnetic debris in the stomach of farm animals. Another objective is to provide such a device that is not subject to corrosion so that it may be reused many times without degradation. A further objective is to provide such a device that has the ability to collect debris preferably at its ends so that as debris is collected it forms a ball thereby reducing the possibility of puncturing the stomach lining of an animal.

Other features and advantages of the present invention will become apparent from the following more detailed description, taken in conjunction with the accompanying drawings, which illustrate, by way of example, the principles of the invention.

BRIEF DESCRIPTION OF THE DRAWING

The accompanying drawings illustrate the present invention. In such drawings.

DETAILED DESCRIPTION OF THE PREFERRED EMBODIMENT

Figure 1:
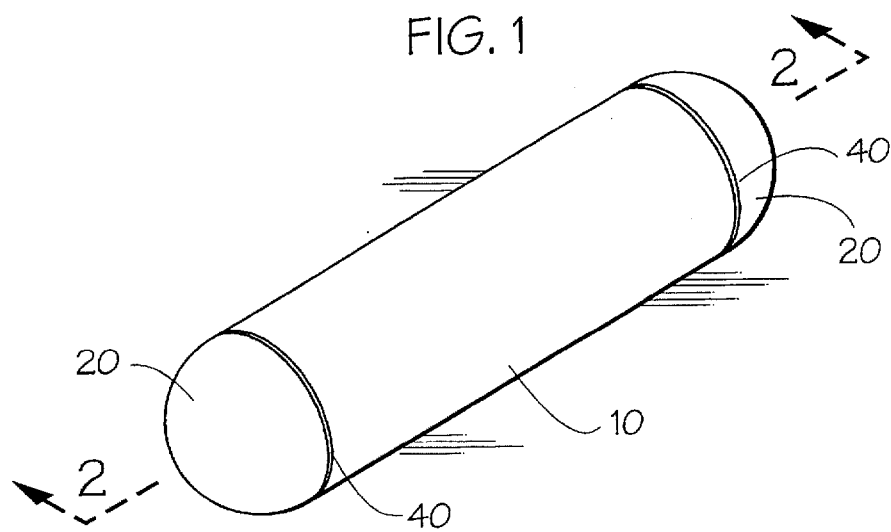
FIG. 1 is a perspective view of the preferred embodiment of the present invention.
Figure 2:
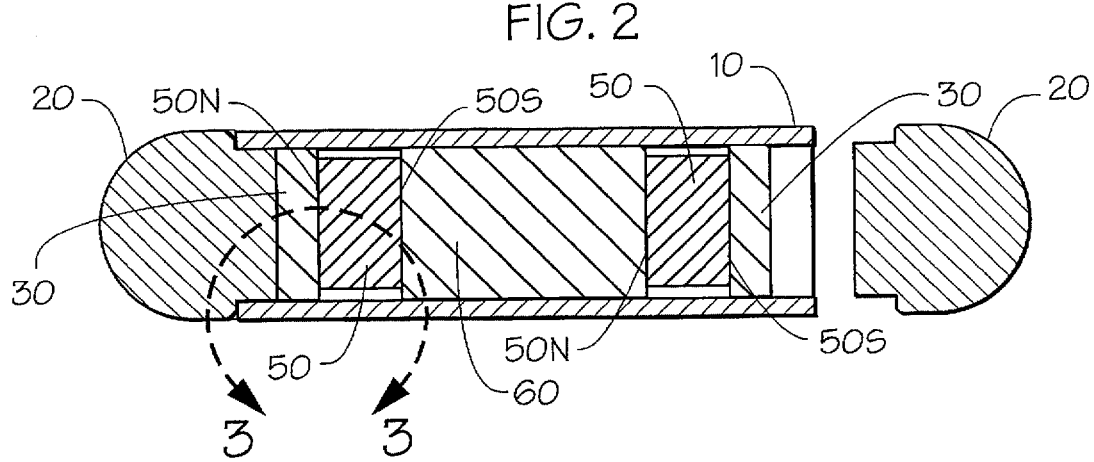
FIG. 2 is a cross-sectional view thereof taken along line 2—2 in FIG. 1 and showing the interior detail of the invention and placement of elements.
Figure 3:
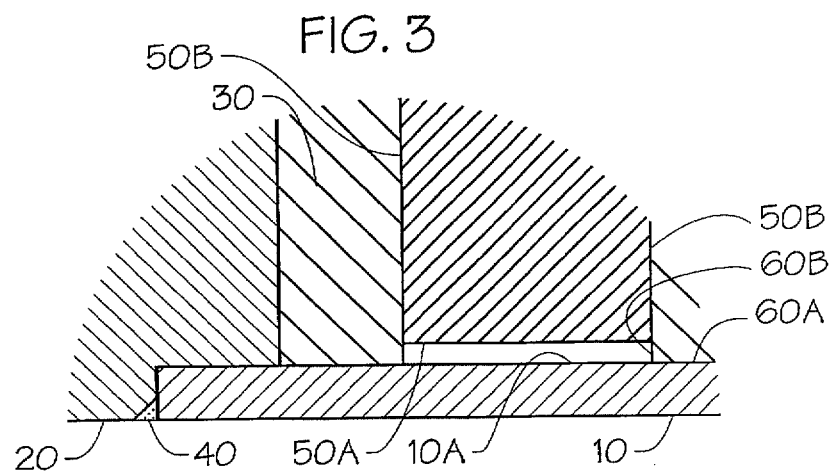
FIG. 3 is an enlarged view of a portion of FIG. 2 taken along line 3—3 thereof, particularly showing the means of joining the end caps of the invention to the case of the invention.

The above described drawing figures illustrate the invention, a magnetic device for capturing magnetically attractive objects in the stomach of an animal. The device provides a hollow, open ended, cylindrical case 10 made of a rigid, corrosion resistant, non-magnetic material such as 316 stainless steel. A rod-shaped, center piece 60 made of an iron bearing material is positioned centrally in the case 10, and has an outside wall 60A in contact with an inside wall 10A of the case 10. A pair of disc-shaped permanent magnetic members 50, preferably made of a Nd—Fe—B alloy, each provide an annular side surface 50A and two opposing end surfaces 50B as shown in FIG. 3. The end surfaces 50B provide a north magnetic pole 50N and a south magnetic pole 50S on each of the magnetic members 50. The magnetic members 50 are positioned within the case 10 so that one side surface 60B of the center piece 60 touches the south magnetic pole 50S of one magnetic member 50, and the other side surface 60B of the center piece 60 touches the north magnetic pole 50N of the other magnetic member 50. A pair of disc-shaped, iron bearing end pieces 30, are positioned within the case, each in contact with one magnetic member 50. A pair of caps 20 made of a rigid, corrosion resistant, non-magnetic material, preferably the 316 stainless steel of the case 10, are tightly fitted to the open ends of the case 10 and are integrally attached to it, preferably by a welding technique providing a weld joint 40 (FIG. 3) in such a manner that gastric juices in the stomach cannot cause corrosion of the caps 20, the case 10, or the joint 40, and cannot enter the case 10. The device is assembled such that movement of the center piece 60, magnetic members 50 and the end pieces 30, within the case, is not possible.

Figure 4:
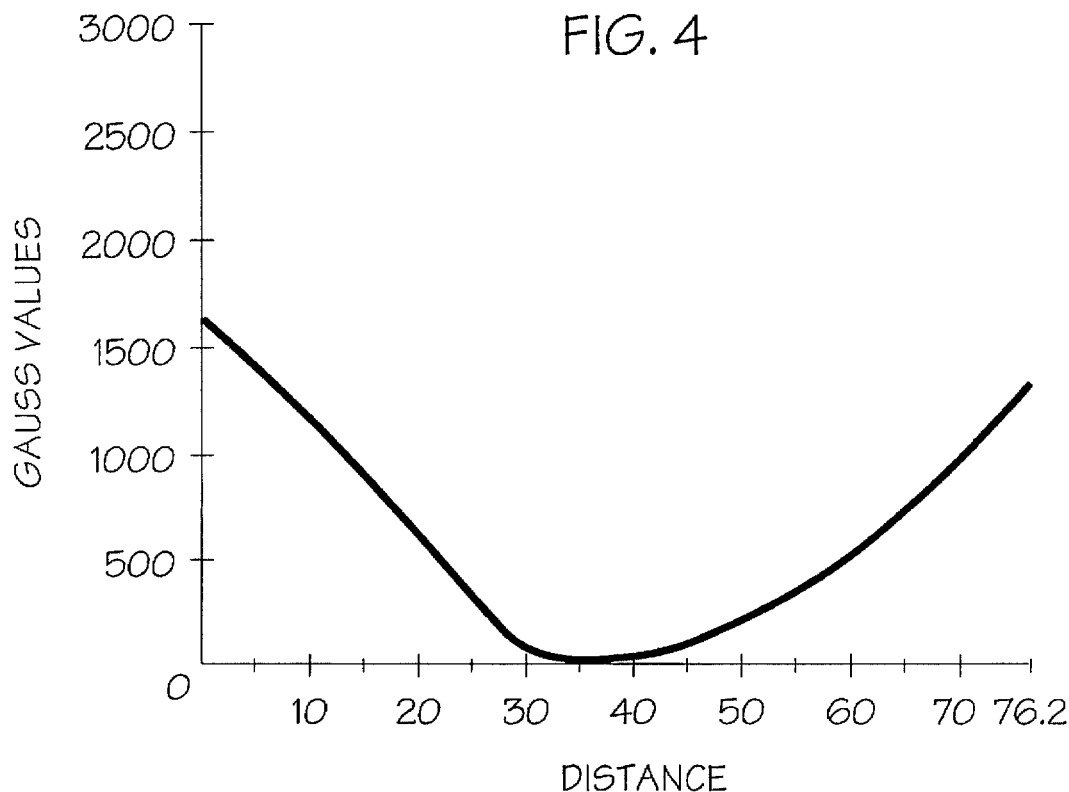
FIG. 4 is an energy (absolute value) versus distance chart for a typical cow pill of the most prevalent type using alnico magnets.
Figure 5:
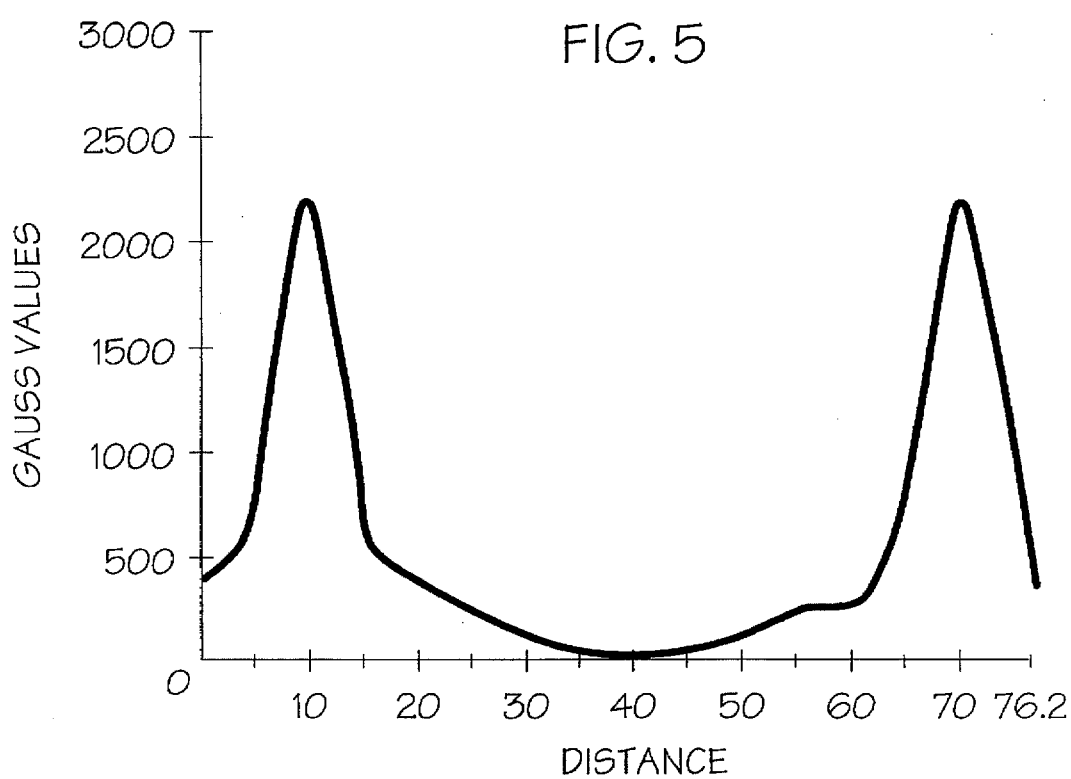
FIG. 5 s an energy (absolute value) versus distance chart for the present invention a 76.2 mm long animal pill type magnetic attraction device.

The present invention is an elongated animal pill type magnetic attraction device for insertion into the stomach of an animal. It is able to attract iron bearing objects that are ingested by the animal so that these objects are not able to damage the animal. The standard "cow pill" in use is an alnico based device having an energy curve as shown in FIG. 4. This standard device has been very successful in achieving its goals in farm animals for years. The present invention improves on the alnico device in three ways. First, the alnico, and also other such devices in the prior art have a high energy near the ends of the pill shape. This results in the strong attraction and holding of sharp metallic objects at these ends which, by their location and placement, and the fact that they are held in place so strongly, causes punctures and ruptures in the stomach of animals and have been known to pierce the animal's heart resulting in death. In the present improved device, the energy at the ends of the device is rather low, so that the accumulation of sharp objects at these ends is eliminated. The second manner of improvement of the present invention over the alnico, as well as the other prior art, is in the use of high energy magnets such that the magnetic attraction capability of the device is significantly greater than many of the magnets shown in the art. The final manner of improvement of the present invention is in the use of only two magnetic members 50, arranged between a center piece 60, where the piece 60 has a length significant with respect to that of the magnetic members 50, and where the piece 60 contacts opposite poles of the magnetic members 50. In this case we find that the piece 60 incorporates a magnetic "dead zone" as seen in FIG. 5 between about 25 mm and 45 mm. This productive use of this dead zone and its functional benefits is a major discovery and invention step in the production of the present improved animal magnetic device. The fact that the present invention provides two annular zones of extremely high magnetic strength separated by a dead zone of significant length, has been found to result in the collection of metal objects near, but not at, the ends of the elongated device. This preferential collection of these metal parts in the two separated "high zones" results in the initial collection of objects at these high zones. As objects collect over time, so that the "high zones" build up layers of objects, it has been found, that further objects then are preferentially collected toward and into the dead zone, and over time this results in the invention device and all of the collected objects forming a ball shaped collection of these objects collected from the stomach. This ball shape provides the maximum volume for incorporating these objects, with the least surface area (a property of the sphere) for the sharp ends of objects to protrude out from for potentially damaging the animal.

The device is preferably elongate in shape with a length to breadth ratio of between about 5 to 1 and 7 to 1. Preferably the center piece has a length equal to approximately one-third of the total length of the device. The foregoing aspect ratio and spacing has been discovered to maximally produce a ball shaped recovery of metallic debris within the stomach.

While the invention has been described with reference to at least one preferred embodiment, it is to be clearly understood by those skilled in the art that the invention is not limited thereto. Rather, the scope of the invention is to be interpreted only in conjunction with the appended claims.

What is claimed is:

1. A magnetic device for attracting magnetically attractive objects in the stomach comprising:

a hollow, cylindrical case made of a rigid, corrosion resistant, non-magnetic material, and having open ends;

a rod-shaped, iron bearing center piece positioned centrally in the case, the center piece having an outside wall in contact with an inside wall of the case;

a pair of disc shaped permanent magnetic members, each of the magnetic members providing an annular side surface and two opposing end surfaces, one said end surface providing a north magnetic pole of said magnetic member, the other said end surface providing a south magnetic pole of said magnetic member;

the magnetic members positioned within the case so that one side surface of the center piece touches the south magnetic pole of one said magnetic member, and the other side surface of the center piece touches the north magnetic pole of the other said magnetic member;

a pair of disc-shaped, iron bearing end pieces, each one of the end pieces being positioned in contact with one said magnetic member;

a pair of caps made of a rigid, corrosion resistant, non-magnetic material, the caps being tightly fitted to the open ends of the case and integrally attached thereto such that gastric juices in the stomach cannot cause corrosion of the caps or the case and cannot enter the case;

the device assembled such that movement of the center piece, magnetic members and the end pieces, within the case is not possible.

2. The device of claim 1 wherein the magnetic members are made of a Nd—Fe—B alloy.

3. The device of claim 1 wherein the device is elongate in shape with a length to breadth ratio of between about 5 to 1 and 7 to 1, and wherein the center piece has a length equal to approximately one-third of the total length of the device, whereby a magnetic field shape results in spherical debris collection on the device.

* * * * *